(12) United States Patent
Choi

(10) Patent No.: US 9,028,489 B2
(45) Date of Patent: May 12, 2015

(54) ELECTRODE FOR RADIOFREQUENCY TISSUE ABLATION

(76) Inventor: Jung-sook Choi, Kyunggi-do (KR)

(*) Notice: Subject to any disclaimer, the term of this patent is extended or adjusted under 35 U.S.C. 154(b) by 2325 days.

(21) Appl. No.: 11/794,065

(22) PCT Filed: Dec. 27, 2005

(86) PCT No.: PCT/KR2005/004585
§ 371 (c)(1),
(2), (4) Date: Dec. 3, 2007

(87) PCT Pub. No.: WO2006/071058
PCT Pub. Date: Jul. 6, 2006

(65) Prior Publication Data
US 2008/0147060 A1    Jun. 19, 2008

(30) Foreign Application Priority Data

Dec. 28, 2004  (KR) .................. 10-2004-0113945

(51) Int. Cl.
*A61B 18/14*    (2006.01)
*A61B 18/00*    (2006.01)

(52) U.S. Cl.
CPC ... *A61B 18/1477* (2013.01); *A61B 2018/00791* (2013.01); *A61B 2018/00023* (2013.01); *A61B 2018/00029* (2013.01)

(58) Field of Classification Search
CPC .......... A61B 18/1477; A61B 2018/00023; A61B 2018/00029; A61B 2018/00714; A61B 2018/00791; A61B 2018/00797; A61B 2018/00815; A61B 2018/00821; A61B 2562/0271
USPC .................. 606/41, 42, 45–47, 49
See application file for complete search history.

(56) References Cited

U.S. PATENT DOCUMENTS

| | | | |
|---|---|---|---|
| 5,335,669 A * | 8/1994 | Tihon et al. ................ 600/549 |
| 6,267,758 B1 | 7/2001 | Daw et al. | |
| 6,322,559 B1 * | 11/2001 | Daulton et al. .............. 606/41 |
| 6,440,127 B2 | 8/2002 | McGovern et al. | |
| 6,613,045 B1 | 9/2003 | Laufer et al. | |
| 6,632,221 B1 * | 10/2003 | Edwards et al. ............. 606/41 |

FOREIGN PATENT DOCUMENTS

JP    2002-301087    10/2002
JP    2004-141273    5/2004

OTHER PUBLICATIONS

International Search Report for PCT/KR2005/004585, filed Apr. 7, 2006.

* cited by examiner

*Primary Examiner* — Michael Peffley
*Assistant Examiner* — Samantha Good
(74) *Attorney, Agent, or Firm* — Mintz Levin Cohn Ferris Glovsky and Popeo, P.C.; Steven M. Jensen

(57) ABSTRACT

The present invention discloses an electrode for radiofrequency tissue ablation which can coagulate and necrotize a tissue by radiofrequency electric energy. The electrode for radiofrequency tissue ablation coagulates and necrotizes a target part of the tissue by sensing a temperature of the tissue. The electrode includes a horn-shaped closed end sharpened to its one end, a hollow tube type electrode extended long in the length direction from the other end of the closed end, an insulation member installed on the outer circumference of the hollow electrode except for the part connected to the closed end, at least one temperature sensor installed on the outer circumference of the hollow electrode to be positioned inside the insulation member, for sensing an ambient temperature, and a control unit connected to the hollow electrode and the temperature sensor, for deciding coagulation and necrosis of the tissue according to the temperature sensed by the temperature sensor, and controlling the output supplied to the hollow electrode.

6 Claims, 11 Drawing Sheets de# ELECTRODE FOR RADIOFREQUENCY TISSUE ABLATION

CROSS REFERENCE TO RELATED APPLICATIONS

This application is the U.S. national phase application, pursuant to 35 U.S.C. §371, of International Patent Application No. PCT/KR2005/004585, having an international filing date of Dec. 27, 2005, designating the U.S., which claims priority to Korean Patent Application Number 10-2004-0113945, having an filing date of Dec. 28, 2004, the contents of which are incorporated herein by reference in their entirety.

BACKGROUND OF THE INVENTION

1. Field of the Invention

The present invention relates to an electrode for radiofrequency tissue ablation which can coagulate and necrotize a tissue by radiofrequency electric energy, and more particularly, to an electrode for radiofrequency tissue ablation which can coagulate and necrotize a target part of a tissue by sensing a temperature of the tissue.

2. Description of Related Art

There has been suggested a method for coagulating or ablating a target tissue with radiofrequency energy by inserting a long hollow tube type electrode into the tissue. Here, a radiofrequency output is transmitted to the tissue to heat the tissue, so that the tissue and blood vessel can be coagulated by more or less complicated biochemical equipment. Such a process is carried out by coagulation of a cell (including tissue, blood vessel and blood) by heat distortion of protein in the cell over about 55° C.

However, the tissue and blood are excessively coagulated and carbonized near the electrode for radiofrequency tissue ablation. Such a carbonized tissue is operated as an insulator interrupting expansion of a tissue coagulation area. In order to solve the above problem, tissues can be coagulated and necrotized in a wide area by lowering a temperature of peripheral tissues by circulating a coolant saline solution in the electrode or externally ejecting the saline solution. In addition, the tissues can be coagulated and necrotized in a wide area by circulating a coolant saline solution and externally ejecting some of the saline solution at the same time.

FIG. 1 is a side-sectional view illustrating a conventional electrode for radiofrequency tissue ablation.

In detail, as illustrated in FIG. 1, the conventional electrode for radiofrequency tissue ablation includes a sharp closed end 10 inserted into a tissue, for generating radiofrequency energy, and a hollow electrode 20 connected to the closed end 10. An insulation coating 24 is coated on the outer circumference of the hollow electrode 20 except for the part connected to the closed end 10. A control unit (not shown) is installed to generate radiofrequency electric energy in the closed end 10 by supplying an output to the closed end 10 and the hollow electrode 20. A hollow refrigerant tube 30 is installed in the hollow electrode 20 with a predetermined gap from the inner circumference of the hollow electrode 20. Cooling water flowing into the refrigerant tube 30 is discharged between the refrigerant tube 30 and the hollow electrode 20 after cooling the closed end 10.

If necessary, a hole 20h is formed on the part of the hollow electrode 20 adjacent to the closed end 10, so that some of the cooling water can be directly injected into the tissue to prevent carbonization of the tissue and expand the electrode area to efficiently coagulate the tissue.

A temperature sensor 22 is installed on the outer circumference of the hollow electrode 20 adjacent to the closed end 10, for sensing a temperature of the closed end 10. According to the sensed temperature, the control unit controls the closed end 10 to generate radiofrequency electric energy for a predetermined time by adjusting the output. Here, the tissue is maintained over a predetermined temperature for a pre-determined time for complete coagulation and necrosis.

However, in the conventional electrode for radiofrequency tissue ablation, since the temperature sensor 22 is installed near the closed end 10 generating radiofrequency electric energy, the temperature sensor 20 can only sense the temperature of the closed end 10 and the temperature of the tissue adjacent to the closed end 10. It is thus difficult to coagulate and necrotize only a target part by maintaining a pre-determined temperature in an accurate ablation part.

SUMMARY OF THE INVENTION

Technical Problem

The present invention is achieved to solve the above problems. An object of the present invention is to provide an electrode for radiofrequency tissue ablation which can coagulate and necrotize only a target part of a tissue by sensing a temperature of the tissue in a part separated from a radiofrequency electric energy generation point by a predetermined gap, and controlling generation of radiofrequency electric energy according to the sensed temperature.

Technical Solution

In order to achieve the above-described object of the invention, there is provided an electrode for radiofrequency tissue ablation, including: a horn-shaped closed end sharpened to its one end; a hollow tube type electrode extended long in the length direction from the other end of the closed end; an insulation member installed on the outer circumference of the hollow electrode except for the part connected to the closed end; at least one temperature sensor installed on the outer circumference of the hollow electrode to be positioned inside the insulation member, for sensing an ambient temperature; and a control unit connected to the hollow electrode and the temperature sensor, for deciding coagulation and necrosis of the tissue according to the temperature sensed by the temperature sensor, and controlling the output supplied to the hollow electrode.

BRIEF DESCRIPTION OF THE DRAWINGS

The present invention will become better understood with reference to the accompanying drawings which are given only by way of illustration and thus are not limitative of the present invention, wherein.

DETAILED DESCRIPTION

An electrode for radiofrequency tissue ablation in accordance with the preferred embodiments of the present invention will now be described in detail with reference to the accompanying drawings.

Figure 1:
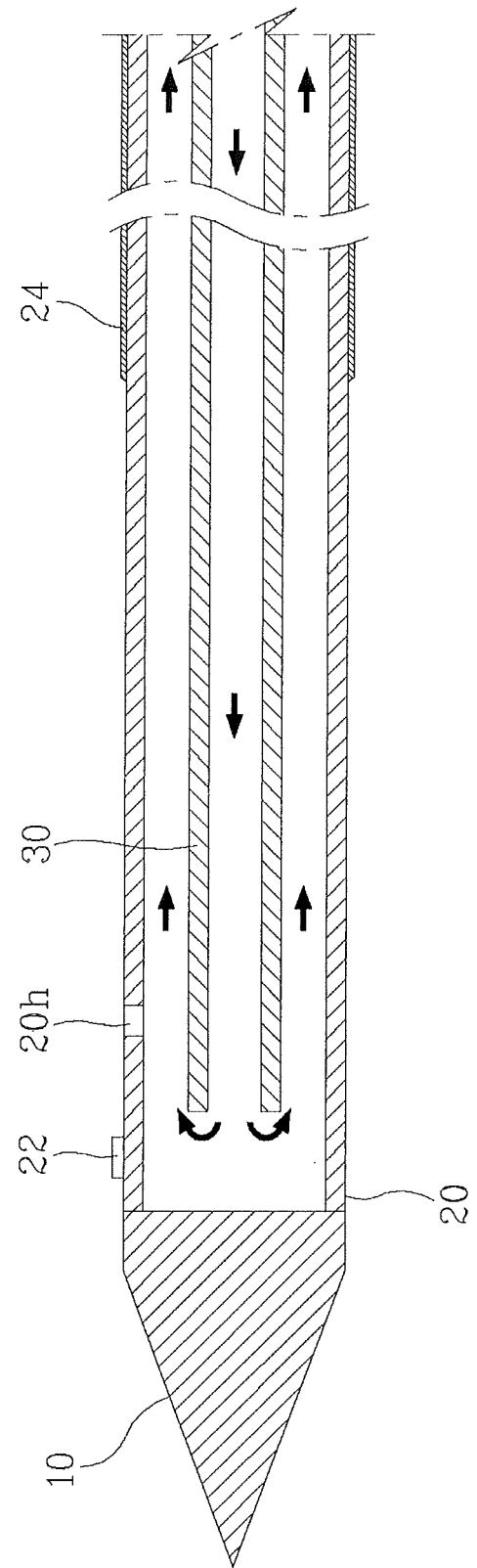
FIG. 1 is a side-sectional view illustrating a conventional electrode for radiofrequency tissue ablation.
Figure 2:
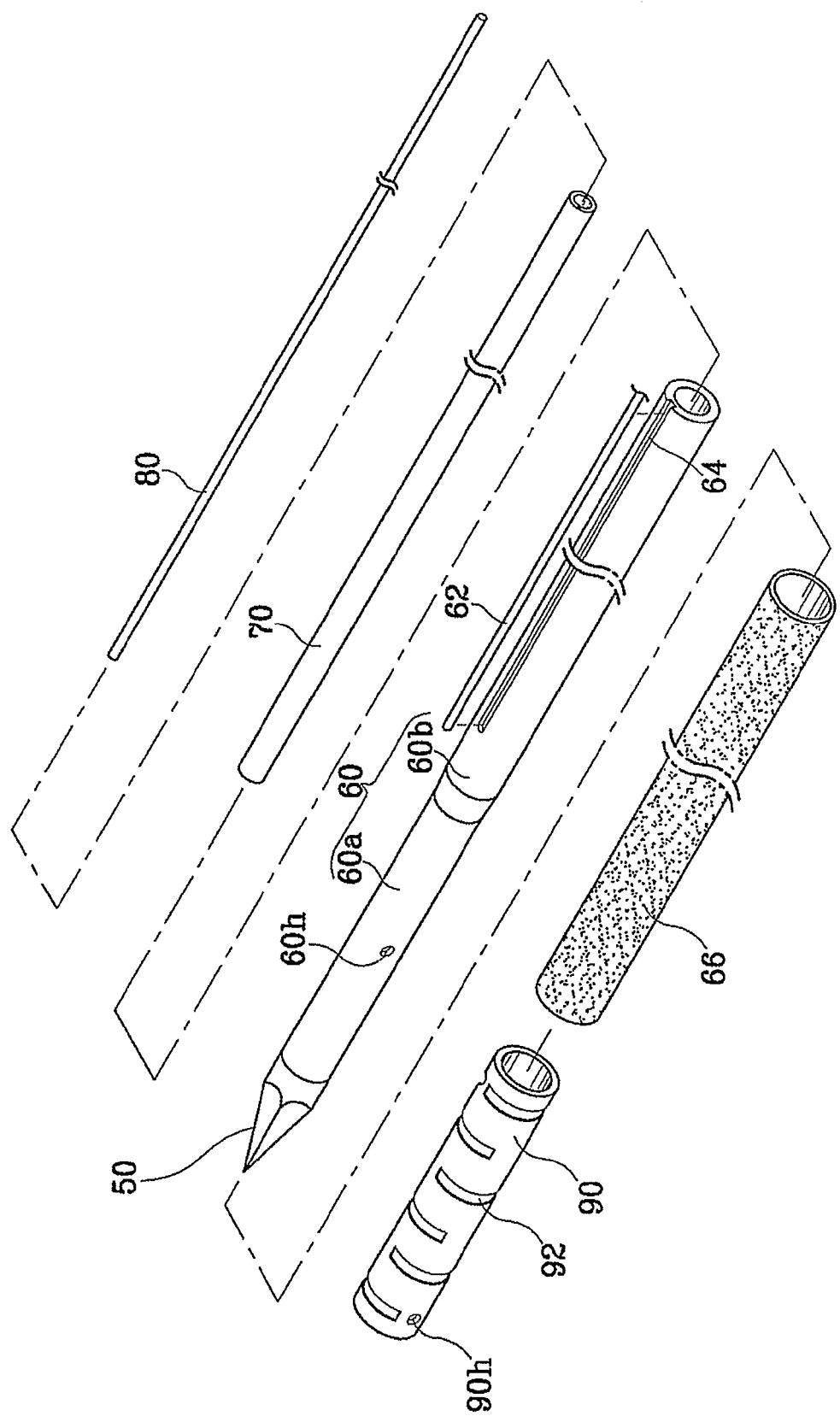
FIG. 2 is a disassembly perspective view illustrating an electrode for radiofrequency tissue ablation in accordance with a first embodiment of the present invention.
Figure 3:
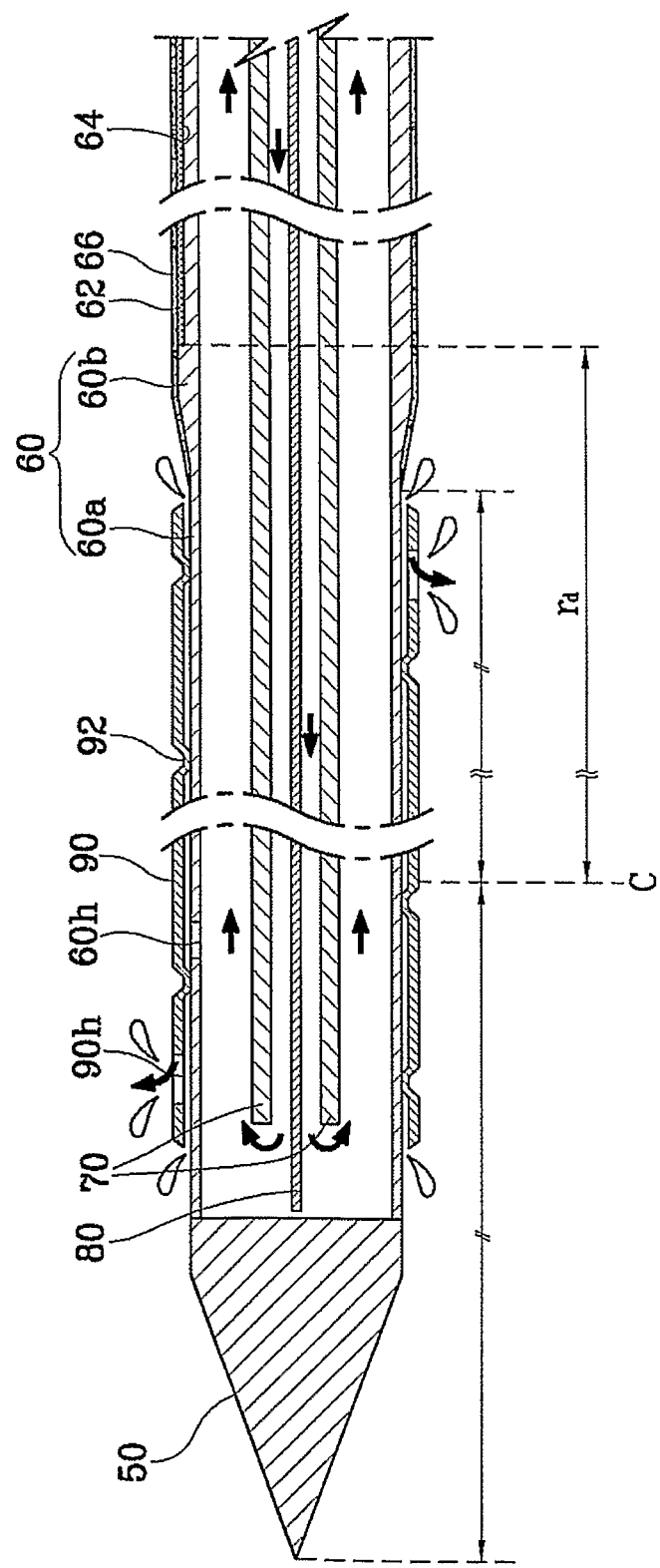
FIG. 3 is a side-sectional view illustrating the electrode for radiofrequency tissue ablation in accordance with the first embodiment of the present invention.

FIGS. 2 and 3 are a disassembly perspective view and a side-sectional view illustrating an electrode for radiofrequency tissue ablation in accordance with a first embodiment of the present invention.

In accordance with the first embodiment of the present invention, referring to FIGS. 2 and 3, a hollow tube type electrode 60 formed long in the length direction and made of a material in which an output (radiofrequency electric energy) flows is connected to a closed end 50 having a sharp end. The hollow electrode 60 is more thickened than the general one. A mounting groove 64 is formed long in the length direction on the outer circumference of the hollow electrode 60 with a predetermined gap from the closed end 50, so that a temperature sensor 62 can be mounted thereon. In a state where the temperature sensor 62 is mounted on the mounting groove 64, an insulation member 66 is covered on the outer circumference of the hollow electrode 60 except for the part connected to the closed end 50.

The electrode for radiofrequency tissue ablation includes a control unit (not shown) for supplying an output to the closed end 50 and the hollow electrode 60. The control unit controls the output supplied to the closed end 50 and the hollow electrode 60 according to the temperature sensed by the temperature sensor 62.

Preferably, the closed end 50 has a sharp end like a triangular pyramid or a circular cone to be easily inserted into the tissue, and is connected to the control unit by a radiofrequency generating wire (not shown) to generate radiofrequency as a whole.

The hollow electrode 60 transmits the output from the control unit to the closed end 50. Since the part of the hollow electrode 60 connected to the closed end 50 is not covered with the insulation member 66, when receiving the output from the control unit, the hollow electrode 60 generates radiofrequency electric energy.

As the closed end 50 and the hollow electrode 60 generate radiofrequency electric energy, the closed end 50 and the hollow electrode 60 may be excessively heated to carbonize the peripheral tissue. The carbonized tissue interrupts transmission of radiofrequency electric energy from the closed end 50 and the hollow electrode 60. In order to solve the foregoing problem, a hollow refrigerant tube 70 is installed in the hollow electrode 60 for circulation of refrigerants.

In detail, the refrigerant tube 70 has a smaller diameter (about 0.8 mm) than the inside diameter of the hollow electrode 60. The end of the refrigerant tube 70 is positioned with a predetermined gap from the closed end 50. A temperature sensor line 80 is inserted into the refrigerant tube 70, for sensing a temperature in the hollow electrode 60 and the closed end area 50, so that the control unit can control output of the electrode or flow of the circulated refrigerants. A supply pipe (not shown) for supplying the refrigerants to the refrigerant tube 70 is connected to the refrigerant tube 70. A discharge pipe (not shown) for discharging the refrigerants between the hollow electrode 60 and the refrigerant tube 70 is connected between the hollow electrode 60 and the refrigerant tube 70.

Accordingly, the refrigerants pressurized by a high pressure (about 700 to 1060 Kpa) are sucked into the refrigerant tube 70 and rapidly transferred between the refrigerant tube 70 and the hollow electrode 60, for cooling the closed end 50 and the part of the hollow electrode 60 contacting the tissue.

Especially, the hollow electrode 60 is divided into a non-insulation unit 60a which is not covered with the insulation member 66 and an insulation unit 60b covered with the insulation member 66. Preferably, the outer circumference of the non-insulation unit 60a is grinded by about 0.3 mm in order to improve cooling efficiency of the non-insulation unit 60a and reduce the diameter of the electrode. The outer circumference of the non-insulation unit 60a and the outer circumference of the insulation unit 60b are smoothly connected to each other to be efficiently inserted into the patient' body in the ablation.

Here, the length of the non-insulation unit 60a is longer than that of the closed end 50 by about five times. For example, the length of the closed end 50 can be 5 mm and the length of the non-insulation unit 60a can be 25 mm.

Some of the refrigerants discharged between the refrigerant tube 70 and the hollow electrode 60 can be directly discharged to the tissue, for preventing carbonization of the peripheral tissue. A hole 60h is formed on the non-insulation unit 60a adjacent to the closed end 50, and a hollow tube 90 for discharging the refrigerants little by little by operating the flow resistance of the refrigerants to prevent excessive ejection of the pressurized refrigerants from the hole 60h covers the hole 60h.

The size of the hollow tube 90 is decided to be inserted onto the non-insulation unit 60a of the hollow electrode 60. The inside diameter of the hollow tube 90 is larger than the outside diameter of the non-insulation unit 60a of the hollow electrode 60 by a pre-determined tolerance. The outside diameter of the hollow tube 90 is identical to that of the insulation unit 60b of the hollow electrode 60. A compressing unit 92 is formed in a zigzag shape on the outer circumference of the hollow tube 90, for forming a path for transferring the refrigerants discharged from the hole 60h of the hollow electrode 60 with the flow resistance. A hole 90h is formed on one side of the hollow tube 90, for directly discharging the decompressed refrigerants to the tissue.

The refrigerants sucked or discharged to/from the hollow electrode 60 and directly discharged to the tissue through the hole 60h are preferably a physiological saline solution which is not harmful to the tissue, for example, 0.9% saline solution, namely, an isotonic solution.

Since the end of the closed end 50 is smoothed, even through the hollow tube 90 is mounted on the non-insulation unit 60a of the hollow electrode 60, the hollow tube 90 and the closed end 50 are smoothly connected to each other. In addition, the hollow tube 90 maintains the identical diameter to that of the insulation unit 60b, so that the electrode can be efficiently inserted into the tissue.

Preferably, the temperature sensor 62 is a thermocouple. The mounting groove 64 is formed long in the length direction on the non-insulation unit 60a of the hollow electrode 60, so that the temperature sensor 62 and the electric wire connected to the temperature sensor 62 can be stably mounted thereon. The mounting groove 64 is formed on the outer circumference of the insulation unit 60b of the hollow electrode 60 separated from the closed end 50 by a predetermined gap with the same depth as the thickness of the temperature sensor 62 and the electric wire.

Preferably, the mounting groove 64 is formed long in the length direction from the point separated from the end of the insulation unit 60b by at least 5 mm. Accordingly, although the temperature sensor 62 is mounted on the end of the mounting groove 64 for sensing the temperature, the temperature sensor 62 is less influenced by the non-insulation unit 60a maintaining a high temperature state by radiofrequency.

Preferably, the temperature sensor 62 is mounted on the position separated in the insulation unit 60b direction from the center C of the length of the closed end 50 and the non-insulation unit 60a by a coagulation and necrosis radius $r_d$. More preferably, the temperature sensor 62 is installed to be movable in the mounting groove 64 in the length direction.

On the other hand, a pair of mounting grooves 64 are formed at an interval of 180 or a plurality of mounting grooves 64 are formed at predetermined intervals on the outer circumference of the insulation unit 60b of the hollow electrode 60. The temperature sensors 62 (not shown) can be installed on the mounting grooves 64 (not shown), respectively. Each of the temperature sensors 62 can be separated in the insulation unit 60b direction from the center C of the length of the closed end 50 and the non-insulation unit 60a by different set values. Preferably, the set values are decided between a minimum radius r and a maximum radius R in consideration of a tolerance of an ablation part.

When the temperature sensor 62 and the electric wire are stably positioned on the mounting groove 64 of the hollow electrode 60, the temperature sensor 62 and the electric wire maintain the same curved surface with the outer circumference of the hollow electrode 60, thereby maintaining the diameter of the electrode as it is. Therefore, the electrode can be efficiently inserted into the tissue.

Since the coagulation and necrosis parts are different in size, it is advantageous to manufacture various electrodes in which the temperature sensors 62 are mounted on different positions of the hollow electrodes 60.

The temperature sensor 62 can directly sense the temperature of the tissue. While the tissue is coagulated and necrotized by radiofrequency electric energy generated by the closed end 50 and the part of the hollow electrode 60, the temperature sensor 62 senses the temperature of the tissue. When the temperature and time conditions are satisfactory in the tissue sensed by the temperature sensor 62, the control unit decides that the target part of the tissue has been completely coagulated and necrotized, and stops supplying radiofrequency energy to the closed end 50 and the hollow electrode 60.

Various temperature and time conditions for completely coagulating and necrotizing tissues have been known. In accordance with the present invention, the temperature condition is set as 55° C. and the time condition is set as 5 minutes.

The insulation member 66 is made of a resin or a polymer insulation tube and covered merely on the insulation unit 60b. The insulation member 66 can be made of an insulation coating having a relatively small thickness.

The ablation for coagulating and necrotizing the tissue by the electrode will now be explained. The electrode is selected in consideration of the installation position of the temperature sensor 62 according to the size of the ablation part, or the installation position of the temperature sensor 62 is set by sliding. The electrode is inserted into the tissue so that the center C of the length of the closed end 50 and the non-insulation unit 60a can be positioned at the center of the ablation part. Since the hollow tube 90 is inserted onto the non-insulation unit 60a having a smaller diameter than the insulation unit 60b, and the outer circumferences of the non-insulation unit 60a and the insulation unit 60b are smoothly connected to each other, the electrode wholly maintains a relatively uniform diameter. Furthermore, since the temperature sensor 62 is mounted to compose the same curved surface with the hollow electrode 60, the electrode can be easily inserted into the tissue without being hooked.

Thereafter, the control unit supplies radiofrequency energy to the electrode. The output is transmitted to the hollow electrode 60 and the closed end 50, thereby generating radiofrequency electric energy. The peripheral tissue is coagulated and necrotized from the elliptical shape to the spherical shape by radiofrequency electric energy. At the same time, the high pressure refrigerants are sucked through the refrigerant tube 70 and discharged between the refrigerant tube 70 and the hollow electrode 60, thereby cooling the closed end 50 and the hollow electrode 60. In addition, some of the refrigerants are discharged to the tissue through the hole 60h of the hollow electrode 60 and the hole 90h of the hollow tube 90, thereby cooling the tissue. Accordingly, the peripheral tissue is not excessively heated and carbonized. Also, the refrigerants are operated as conductors for transmitting radiofrequency electric energy to the tissues in a wide area. As a result, a relatively large ablation part can be rapidly coagulated and necrotized.

Here, the control unit supplies the output so that the temperature sensed by the temperature sensor 62 can be maintained over about 55° C. for 5 minutes. If the above condition is satisfied, the control unit decides that the ablation part has been completely coagulated and necrotized, and stops supplying radiofrequency energy.

The electrode can be inserted into the accurate part of the tissue with the help of the laparoscope, transvaginal ultrasound and hysteroscope. For example, when the operator intends to insert the electrode into the target part of the liver cancer tissue, he/she preferably carries out the ablation with the help of the abdominal ultrasound. In the case that the operator inserts the electrode into a target part of an uterus myoma tissue, he/she can carry out the ablation with the help of the laparoscope, or by searching the accurate position of the uterus myoma tissue by the transvaginal ultrasound or hysteroscope, and inserting the electrode into the target part by an adapter adhered to the equipment or an operation space provided to the equipment. The electrodes discussed later are used in the same manner.

Figure 4:
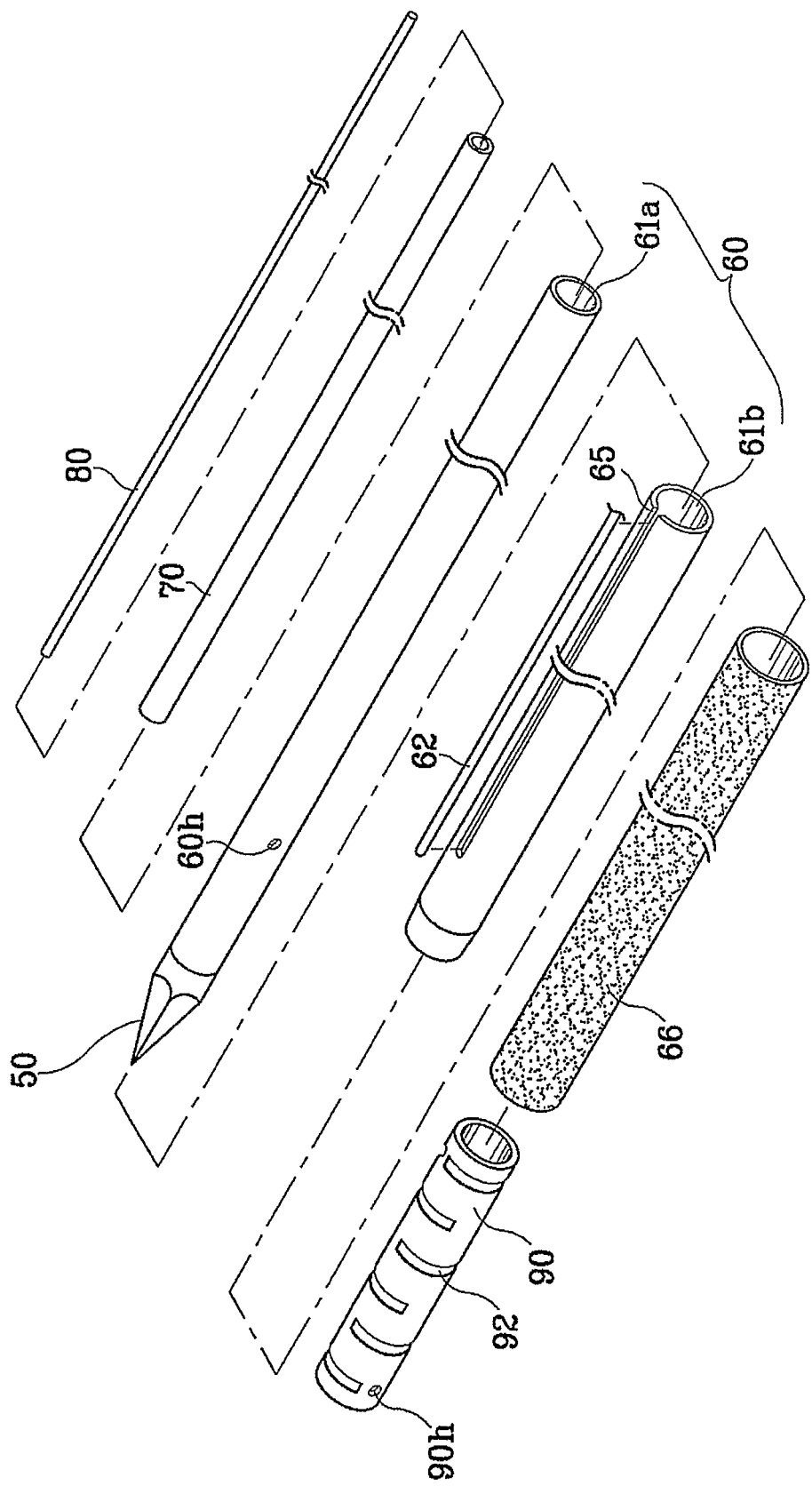
FIG. 4 is a disassembly perspective view illustrating an electrode for radiofrequency tissue ablation in accordance with a second embodiment of the present invention.
Figure 5:
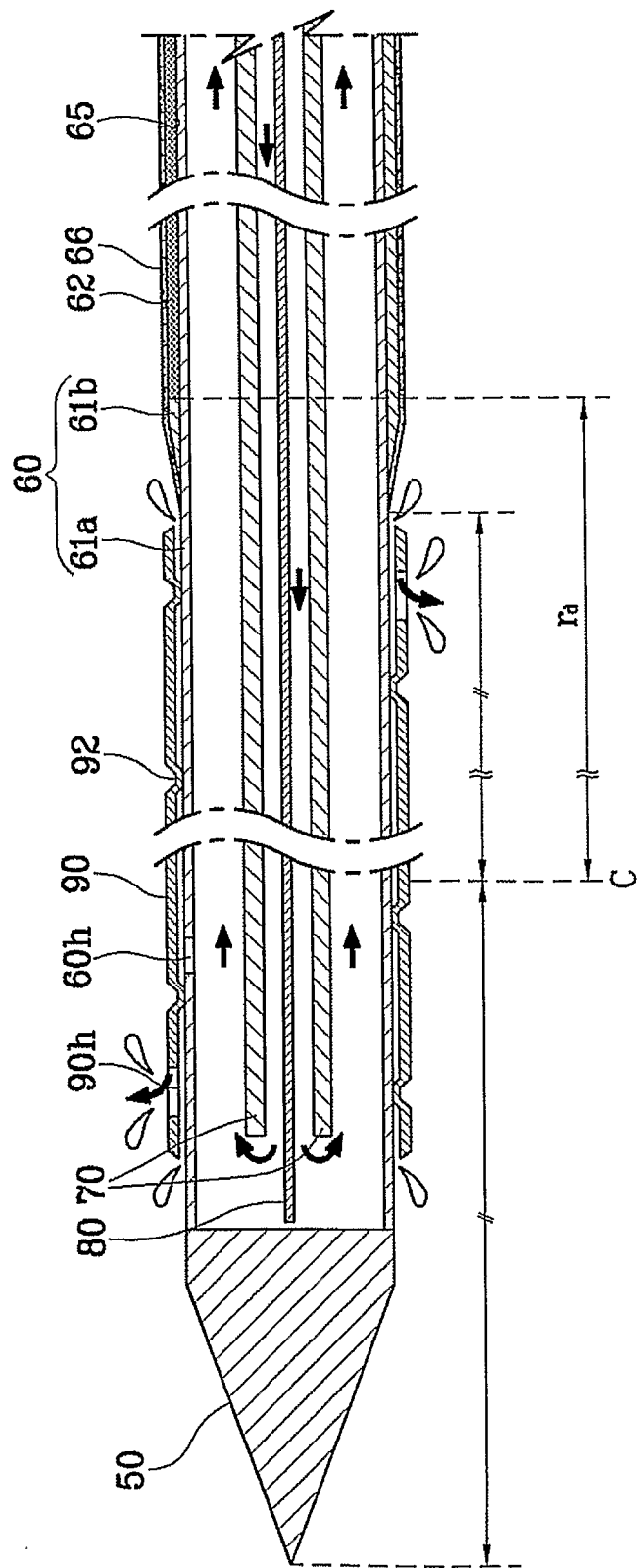
FIG. 5 is a side-sectional view illustrating the electrode for radiofrequency tissue ablation in accordance with the second embodiment of the present invention.

FIGS. 4 and 5 are a disassembly perspective view and a side-sectional view illustrating an electrode for radiofrequency tissue ablation in accordance with a second embodiment of the present invention.

The second embodiment of the present invention is almost identical to the first embodiment described above. As illustrated in FIGS. 4 and 5, the hollow electrode 60 includes two hollow tubes, namely, an inner tube 61a and an outer tube 61b. The closed end 50 is coupled to the end of the inner tube

61a, and the outer tube 61b is installed with a predetermined gap from the closed end 50. The temperature sensor 62 and the electric wire are installed on a mounting hole 65 formed on the outer tube 61b to be connected to the control unit. The insulation member 66 is covered on the whole outer circumference of the outer tube 61b.

Here, the inner tube 61a is a hollow tube having a smaller thickness than the general electrode. The closed end 50 is coupled to the end of the inner tube 61a by soldering or the like.

The refrigerant tube 70 and the temperature sensor line 80 are installed in the inner tube 61a, so that high pressure refrigerants can be sucked or discharged for cooling. The hole 60h is formed on one side end of the inner tube 61a adjacent to the closed end 50, and the hollow tube 90 is installed to transfer the high pressure refrigerants to the tissue through the frictional path little by little. Thus, cooling efficiency is improved, and radiofrequency electric energy is transmitted to a wider area.

The inside diameter of the outer tube 61b is identical to the outside diameter of the inner tube 61a, so that the outer tube 61b can be inserted onto the inner tube 61a. Preferably, one side end of the outer tube 61b is smoothed so that the outer circumferences of the inner tube 61a and the outer tube 61b can be smoothly connected to each other when the outer tube 61b is inserted onto the inner tube 61a.

Since the hollow tube 90 having the same outside diameter as that of the outer tube 61b is inserted onto the inner tube 61a, the outer circumferences of the inner tube 61a and the outer tube 61b need not to be specially smoothed.

In spite of radiofrequency electric energy, the inner tube 61a having a small thickness can be easily cooled by the refrigerants circulated therein and the refrigerants sprayed to the tissue, thereby preventing carbonization of the tissue and coagulating and necrotizing the tissue in a wide area by radiofrequency electric energy. Here, the outer tube 61b is inserted onto most of the inner tube 61a, which reinforces intensity of the electrode in spite of small thickness of the inner tube 61a and large length of the whole electrode.

The slit type mounting hole 65 is formed from the position separated from one side end of the outer tube 61b by at least 5 mm to the other side end. Therefore, when the temperature sensor 62 is mounted on the mounting hole 65, the temperature sensor 62 is less influenced by radiofrequency energy generated at the part of the inner tube 61a which is not covered with the insulation member 66.

The length of the part of the inner tube 61a is larger than that of the closed end 50 by about five times. For example, when the length of the closed end 50 is 5 mm, the length of the part of the inner tube 61a which is not covered with the outer tube 61b is 25 mm.

Preferably, the temperature sensor 62 is mounted on the position separated in the outer tube 61b direction from the center C of the length of the closed end 50 and the inner tube 61a which is not covered with the insulation member 66 by the ablation radius $r_d$. More preferably, the temperature sensor 62 is installed to be movable in the mounting hole 65 in the length direction.

A pair of mounting holes 65 are formed at an interval of 180 or a plurality of mounting holes 65 are formed at predetermined intervals on the outer tube 61b. The temperature sensors 62 (not shown) can be installed on the mounting holes 65 (not shown), respectively. Each of the temperature sensors 62 can be separated in the outer tube 61b direction from the center C of the length of the closed end 50 and the inner tube 61a which is not covered with the insulation member 66 by different set values. Preferably, the set values are decided between the minimum radius r and the maximum radius R in consideration of the tolerance of the ablation part.

The closed end 50, the temperature sensor 62, the insulation member 66, the refrigerant tube 70, the temperature sensor line 80 and the hollow tube 90 of the second embodiment are identical to those of the first embodiment, and thus detailed explanations thereof are omitted. The operation of the whole electrode will now be explained.

The electrode is selected in consideration of the installation position of the temperature sensor 62 according to the size of the ablation part, or the installation position of the temperature sensor 62 is set by sliding. The electrode is inserted into the tissue so that the center C of the length of the closed end 50 and the inner tube 61a which is not covered with the insulation member 66 can be positioned at the center of the ablation part. Since the hollow tube 90 and the outer tube 61b having the same outside diameter are inserted onto the inner tube 61a, the outer circumferences thereof are smoothly connected to each other. Thus, the electrode wholly maintains a relatively uniform diameter. Furthermore, since the temperature sensor 62 is mounted to compose the same curved surface with the hollow electrode 60, the electrode can be easily inserted into the tissue without causing any damages to the tissue.

Thereafter, the control unit supplies radiofrequency energy to the electrode. The output is transmitted to the hollow electrode 60 and the closed end 50, thereby generating radiofrequency electric energy in the closed end 50 and the part of the inner tube 61a. The peripheral tissue is coagulated and necrotized from the elliptical shape to the spherical shape by radiofrequency electric energy. At the same time, the high pressure refrigerants are sucked through the refrigerant tube 70 and discharged between the refrigerant tube 70 and the hollow electrode 60, thereby cooling the closed end 50 and the hollow electrode 60. In addition, some of the refrigerants are discharged to the tissue through the hole 60h of the hollow electrode 60 and the hole 90h of the hollow tube 90, thereby cooling the tissue. Accordingly, the peripheral tissue is not excessively heated and carbonized. Also, the refrigerants are operated as conductors for transmitting radiofrequency electric energy to the tissues in a wide area. As a result, a relatively large ablation part can be rapidly coagulated and necrotized.

Here, the control unit supplies the output so that the temperature sensed by the temperature sensor 62 can be maintained over about 55° C. for 5 minutes. If the above condition is satisfied, the control unit decides that the ablation part has been completely coagulated and necrotized, and stops supplying radiofrequency energy.

Figure 6:
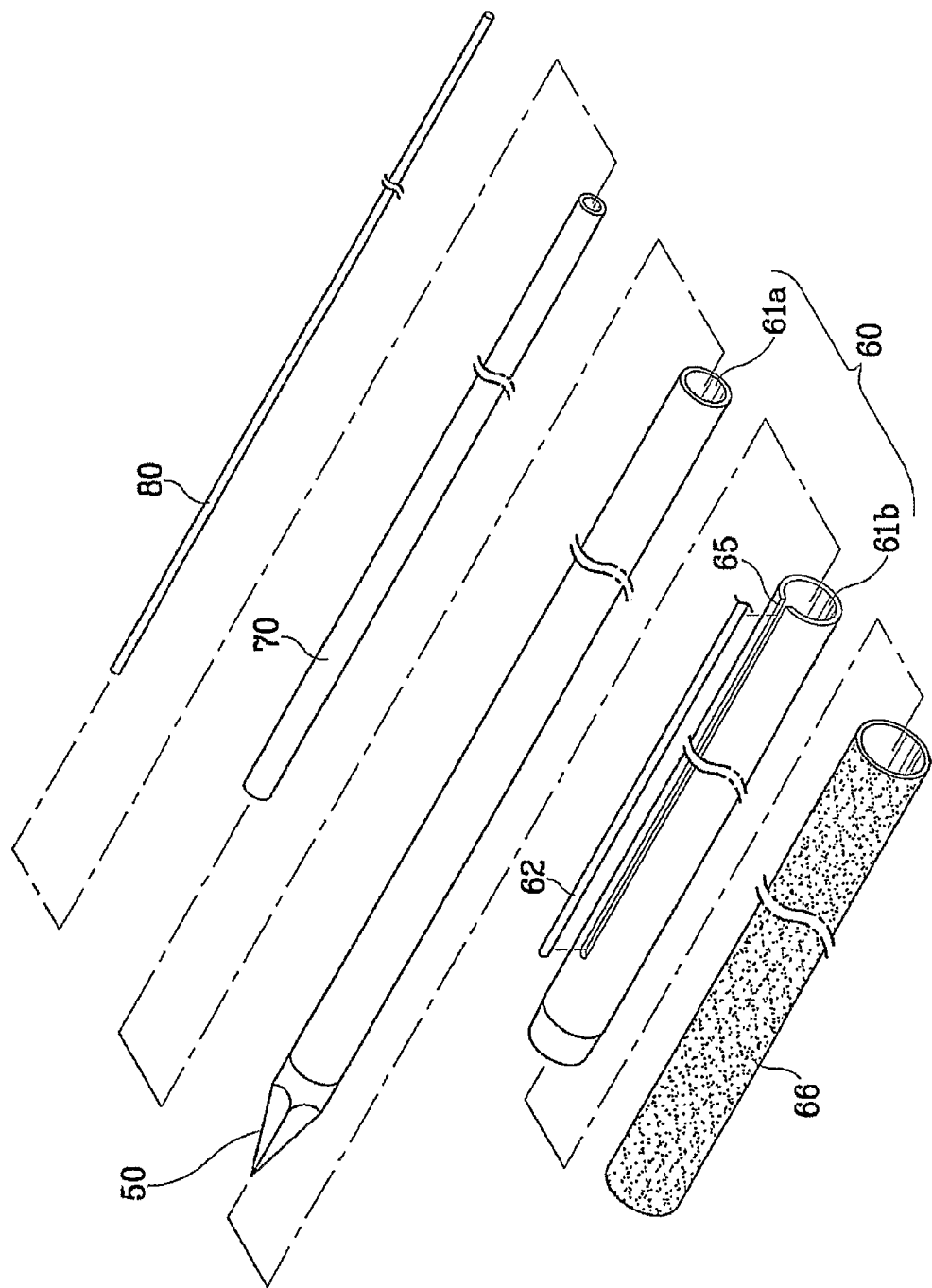
FIG. 6 is a disassembly perspective view illustrating an electrode for radiofrequency tissue ablation in accordance with a third embodiment of the present invention.
Figure 7:
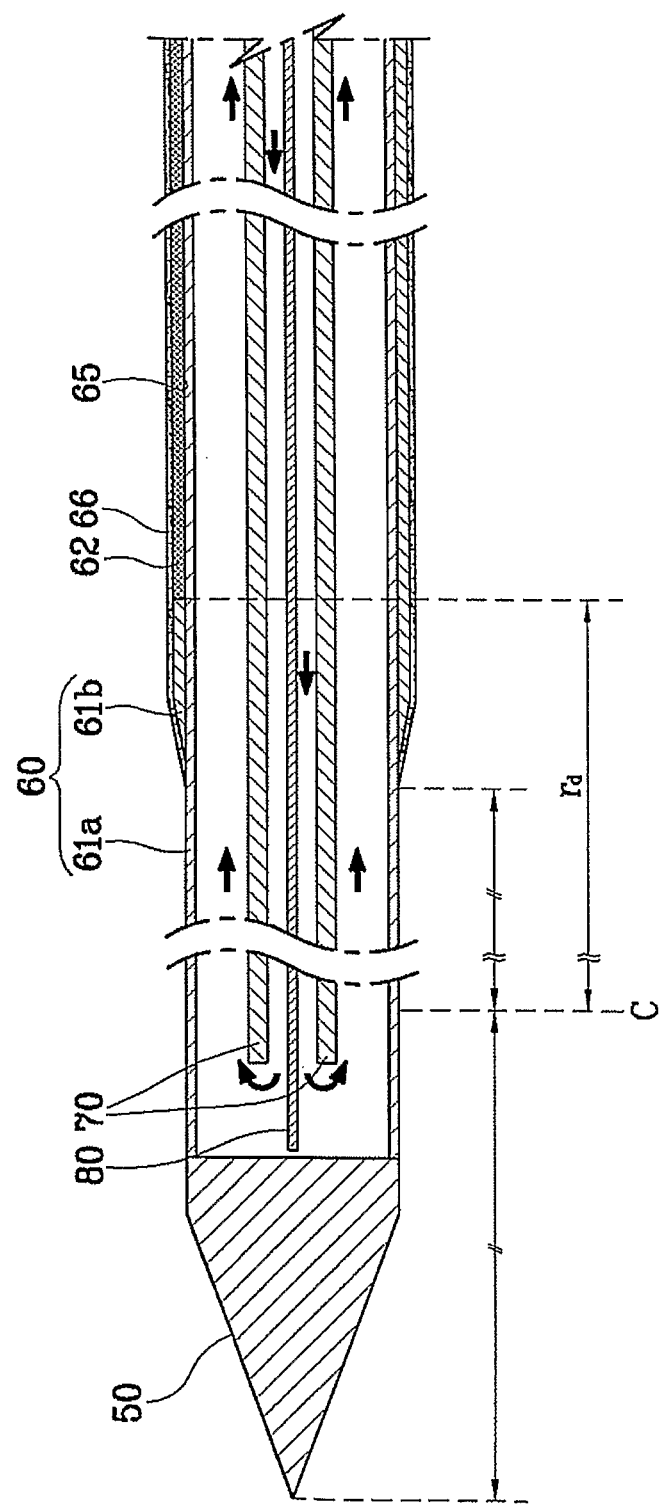
FIG. 7 is a side-sectional view illustrating the electrode for radiofrequency tissue ablation in accordance with the third embodiment of the present invention.

FIGS. 6 and 7 are a disassembly perspective view and a side-sectional view illustrating an electrode for radiofrequency tissue ablation in accordance with a third embodiment of the present invention.

The third embodiment of the present invention is almost identical to the second embodiment described above. As shown in FIGS. 6 and 7, the closed end 50 is coupled to the end of the inner tube 61a, and the outer tube 61b on which the mounting hole 65 is formed is installed to cover the outer circumference of the inner tube 61a with a pre-determined gap from the closed end 50. The temperature sensor 62 and the electric wire are installed on the mounting hole 65 formed on the outer tube 61b to be connected to the control unit. The insulation member 66 is covered on the whole outer circumference of the outer tube 61b. The part of the inner tube 61a which is not covered with the insulation member 66 generates radiofrequency electric energy, thereby coagulating and necrotizing the peripheral tissue. The refrigerant tube 70 and the temperature sensor line 80 are installed, so that high pressure refrigerants can be sucked or discharged to cool the part of the inner tube 61a generating radiofrequency electric energy.

A special hollow tube is not inserted onto the inner tube 61a. One side end of the outer tube 61b is preferably smoothed, so that the outer circumferences of the inner tube 61a and the outer tube 61b can be smoothly connected to each other when the outer tube 61b is mounted on the inner tube 61a to compose the hollow electrode 60.

The closed end 50, the temperature sensor 62, the insulation member 66, the refrigerant tube 70 and the temperature sensor line 80 of the third embodiment are identical to those of the second embodiment, and thus detailed explanations thereof are omitted. The operation of the whole electrode will now be explained.

The electrode is selected in consideration of the installation position of the temperature sensor 62 according to the size of the ablation part, or the installation position of the temperature sensor 62 is set by sliding. The electrode is inserted into the tissue so that the center C of the length of the closed end 50 and the inner tube 61a which is not covered with the insulation member 66 can be positioned at the center of the ablation part. Since the outer circumferences of the inner tube 61a and the outer tube 61b are smoothly connected to each other, the electrode wholly maintains a relatively uniform diameter. Furthermore, since the temperature sensor 62 is mounted to compose the same curved surface with the hollow electrode 60, the electrode can be easily inserted into the tissue without being hooked.

Thereafter, the control unit supplies radiofrequency energy to the electrode. The output is transmitted to the hollow electrode 60 and the closed end 50, thereby generating radiofrequency electric energy in the closed end 50 and the part of the inner tube 61a. The peripheral tissue is coagulated and necrotized from the elliptical shape to the spherical shape by radiofrequency electric energy. At the same time, the high pressure refrigerants are sucked through the refrigerant tube 70 and discharged between the refrigerant tube 70 and the hollow electrode 60, thereby cooling the closed end 50 and the hollow electrode 60. Accordingly, the peripheral tissue is not excessively heated and carbonized, so that the tissues can be coagulated and necrotized in a wide area.

Here, the control unit supplies the output so that the temperature sensed by the temperature sensor 62 can be maintained over about 55° C. for 5 minutes. If the above condition is satisfied, the control unit decides that the ablation part has been completely coagulated and necrotized, and stops supplying radiofrequency energy.

Figure 8:
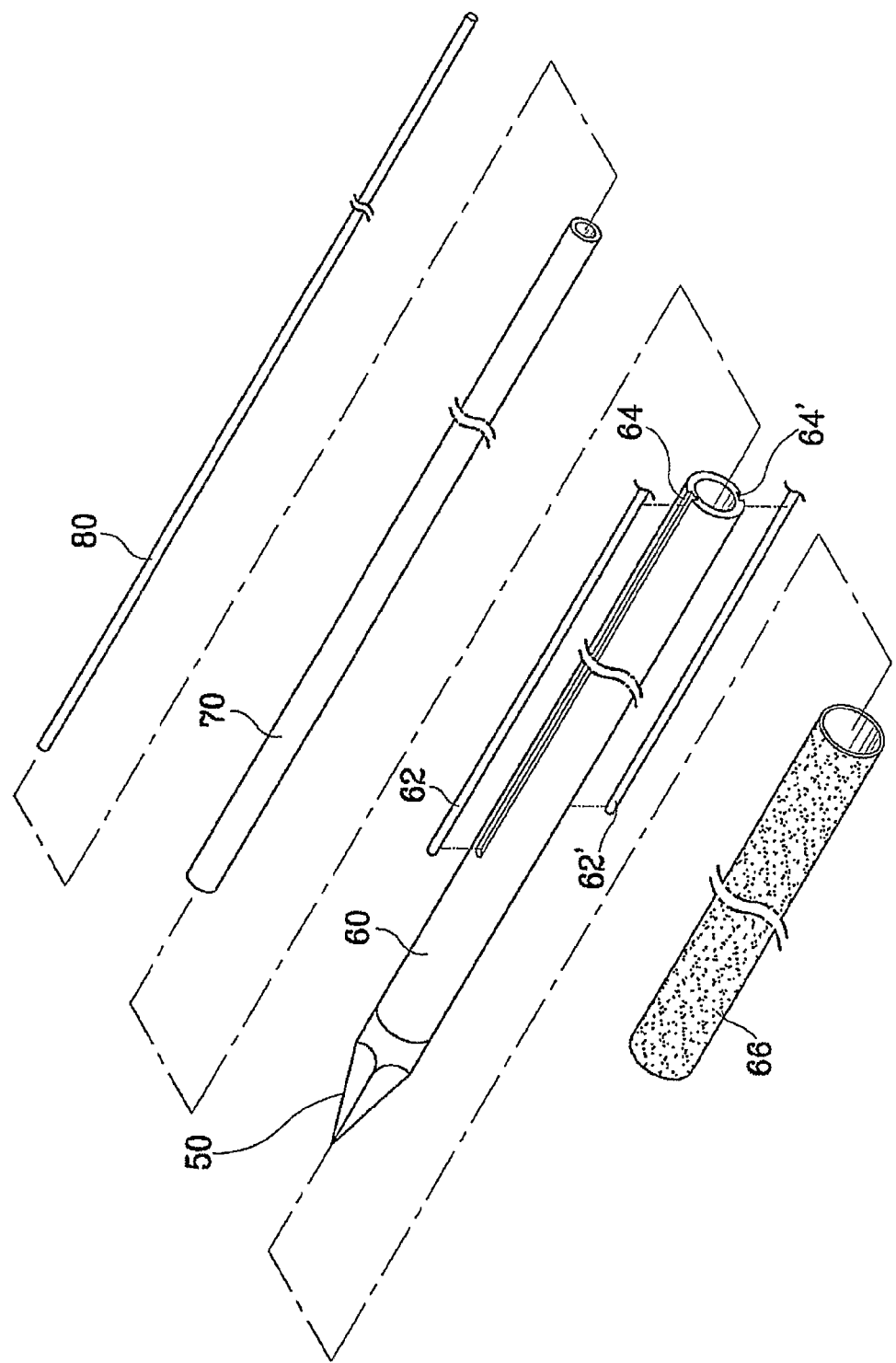
FIG. 8 is a disassembly perspective view illustrating an electrode for radiofrequency tissue ablation in accordance with a fourth embodiment of the present invention.
Figure 9:
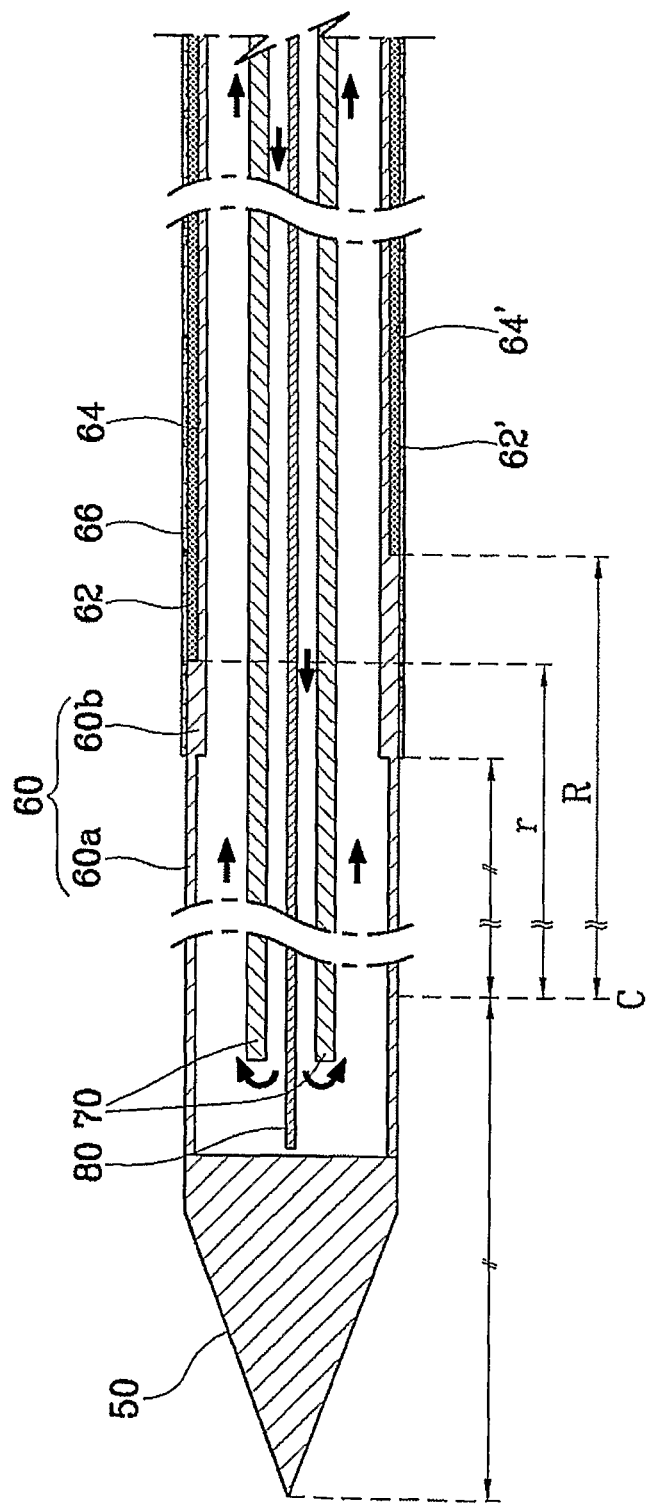
FIG. 9 is a side-sectional view illustrating the electrode for radiofrequency tissue ablation in accordance with the fourth embodiment of the present invention.

FIGS. 8 and 9 are a disassembly perspective view and a side-sectional view illustrating an electrode for radiofrequency tissue ablation in accordance with a fourth embodiment of the present invention.

The fourth embodiment of the present invention is almost identical to the third embodiment described above. As depicted in FIGS. 8 and 9, the hollow electrode 60 includes the non-insulation unit 60a formed in a hollow tube shape at one side end connected to the closed end 50, and the insulation unit 60b covered with the insulation member 66. Even though the non-insulation unit 60a and the insulation unit 60b have the same outside diameter, the non-insulation unit 60a is grinded to have a larger inside diameter than the insulation unit 60b. The mounting grooves 64 and 64 are formed long in the length direction on the outer circumference of the insulation unit 60b. The temperature sensors 62 and 62 and the electric wires are installed on the mounting grooves 64 and 64 to be connected to the control unit. The insulation member 66 is covered on the whole outer circumference of the insulation unit 60b. Only the non-insulation unit 60a generates radiofrequency electric energy, thereby coagulating and necrotizing the peripheral tissue. The refrigerant tube 70 and the temperature sensor line 80 are inserted into the hollow electrode 60, so that high pressure refrigerants can be sucked or discharged to cool the non-insulation unit 60a generating radiofrequency electric energy.

Here, the hollow electrode 60 is a hollow tube thicker than the general hollow electrode. The inner circumference of one side end of the hollow electrode 60 connected to the closed end 50 is grinded to be thinned, for composing the non-insulation unit 60a. The other part of the hollow electrode 60 composes the insulation unit 60b. The mounting grooves 64 and 64 are formed long in the length direction on the outer circumference of the insulation unit 60b with a predetermined gap from the closed end 50. Although the temperature sensors 62 and 62 are mounted on the mounting grooves 64 and 64' the temperature sensors 62 and 62 compose the same curved surface with the outer circumference of the insulation unit 60b.

As the non-insulation unit 60a is thinner than the insulation unit 60b, cooling efficiency by the circulated refrigerants can be improved in spite of radiofrequency electric energy. Since the insulation unit 60b occupying the large part of the whole electrode is thicker than the non-insulation unit 60a, when the electrode is inserted into the ablation part, intensity can be improved.

On the insulation unit 60b, one of the mounting grooves 64 and 64 can be formed, the pair of mounting grooves 64 and 64 can be formed in the circumference direction at an interval of 180° or more than two mounting grooves 64 and 64' can be formed in the circumference direction at predetermined intervals. The temperature sensors 62 and 62' can be installed on the mounting grooves 64 and 64' respectively. Each of the temperature sensors 62 and 62' is installed in different positions within the ablation range considering a predetermined tolerance, for precisely sensing the temperature of the tissue and deciding coagulation and necrosis of the tissue.

Preferably, the mounting grooves 64 and 64' are formed from the point separated from the end of the insulation unit 60b by at least 5 mm, so that the temperature sensors 62 and 62' can be less influenced by heat generated by the non-insulation unit 60a. The temperature sensors 62 and 62' are mounted inside the mounting grooves 64 and 64' The temperature sensors 62 and 62' are installed on the position separated from the center C of the length of the closed end 50 and the non-insulation unit 60a by different set values r and R within the radius range considering a tolerance of an ablation part. When the temperature sensors 62 and 62' are maintained over 55° C. for 5 minutes, the control unit decides that the ablation part has been completely coagulated and necrotized, and stops generating radiofrequency electric energy.

Various kinds of electrodes are manufactured according to the installation positions of the temperature sensors 62 and 62' In addition, one electrode can be used for various sizes of ablation parts, by installing the temperature sensors 62 and 62' to slide in the length direction.

The closed end 50, the insulation member 66, the refrigerant tube 70 and the temperature sensor line 80 of the fourth embodiment are identical to those of the third embodiment, and thus detailed explanations thereof are omitted. The operation of the whole electrode will now be explained.

The electrode is selected in consideration of the installation position of the temperature sensors 62 and 62' according to the size of the ablation part, or the installation positions of the temperature sensors 62 and 62' are set by sliding. The electrode is inserted into the tissue so that the center C of the length of the closed end 50 and the non-insulation unit 60*a* can be positioned at the center of the ablation part. Even through the insulation member 66 is covered on the insulation unit 60*b*, since the outer circumferences of the non-insulation unit 60*a* and the insulation unit 60*b* maintain the same curved surface, the electrode can be easily inserted into the tissue without being hooked.

Thereafter, the control unit supplies radiofrequency energy to the electrode. The output is transmitted to the hollow electrode 60 and the closed end 50, thereby generating radiofrequency electric energy in the closed end 50 and the non-insulation unit 60*a*. The peripheral tissue is coagulated and necrotized from the elliptical shape to the spherical shape by radiofrequency electric energy. At the same time, the high pressure refrigerants are sucked through the refrigerant tube 70 and discharged between the refrigerant tube 70 and the hollow electrode 60, thereby cooling the closed end 50 and the hollow electrode 60. Accordingly, the peripheral tissue is not excessively heated and carbonized, so that the tissues can be coagulated and necrotized in a wide area.

Here, the control unit supplies the output so that the temperatures sensed by the temperature sensors 62 and 62' can be maintained over about 55° C. for 5 minutes. If the above condition is satisfied, the control unit decides that the ablation part has been completely coagulated and necrotized, and stops supplying radiofrequency electric energy.

Figure 10:
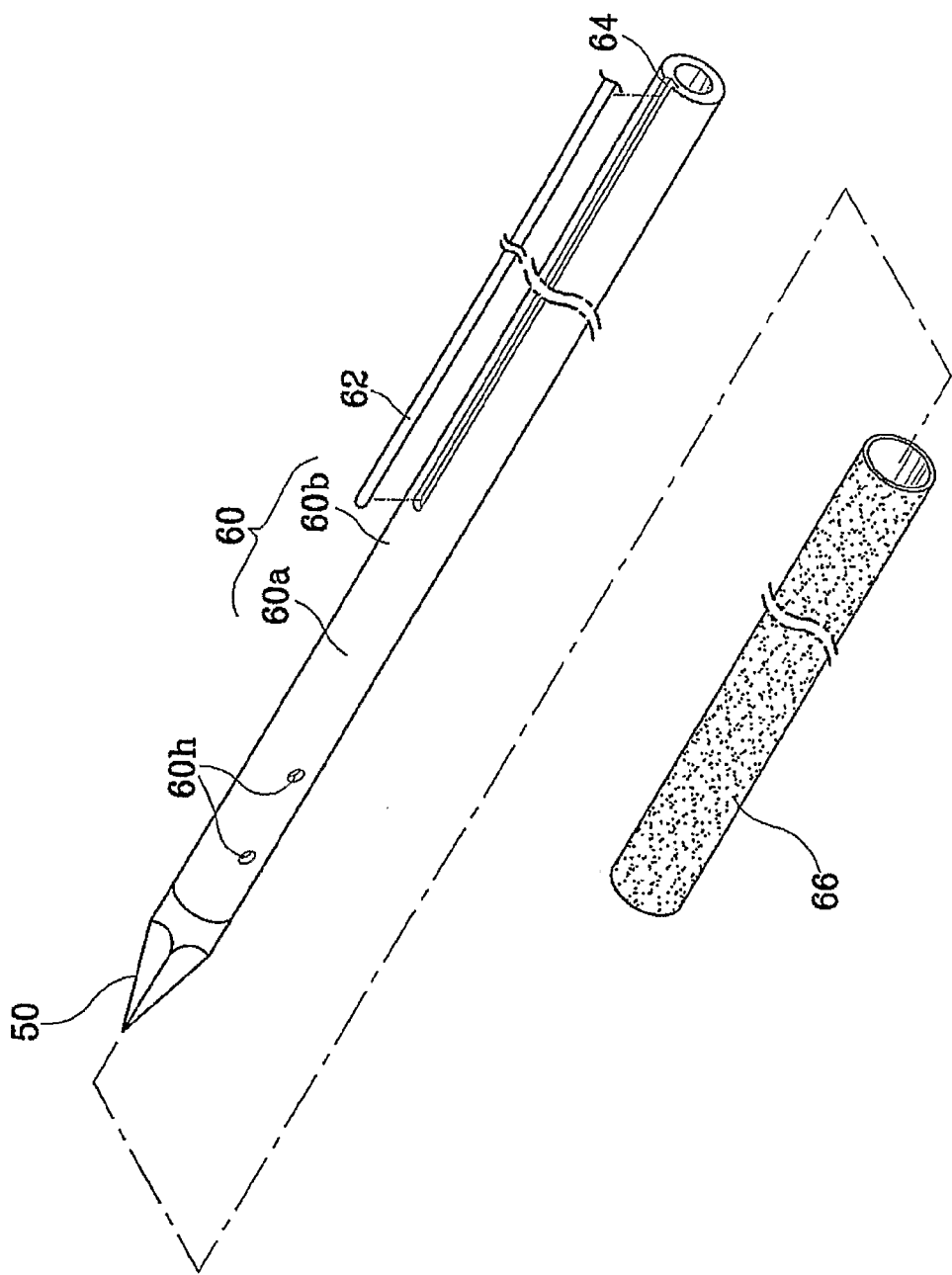
FIG. 10 is a disassembly perspective view illustrating an electrode for radiofrequency tissue ablation in accordance with a fifth embodiment of the present invention.
Figure 11:
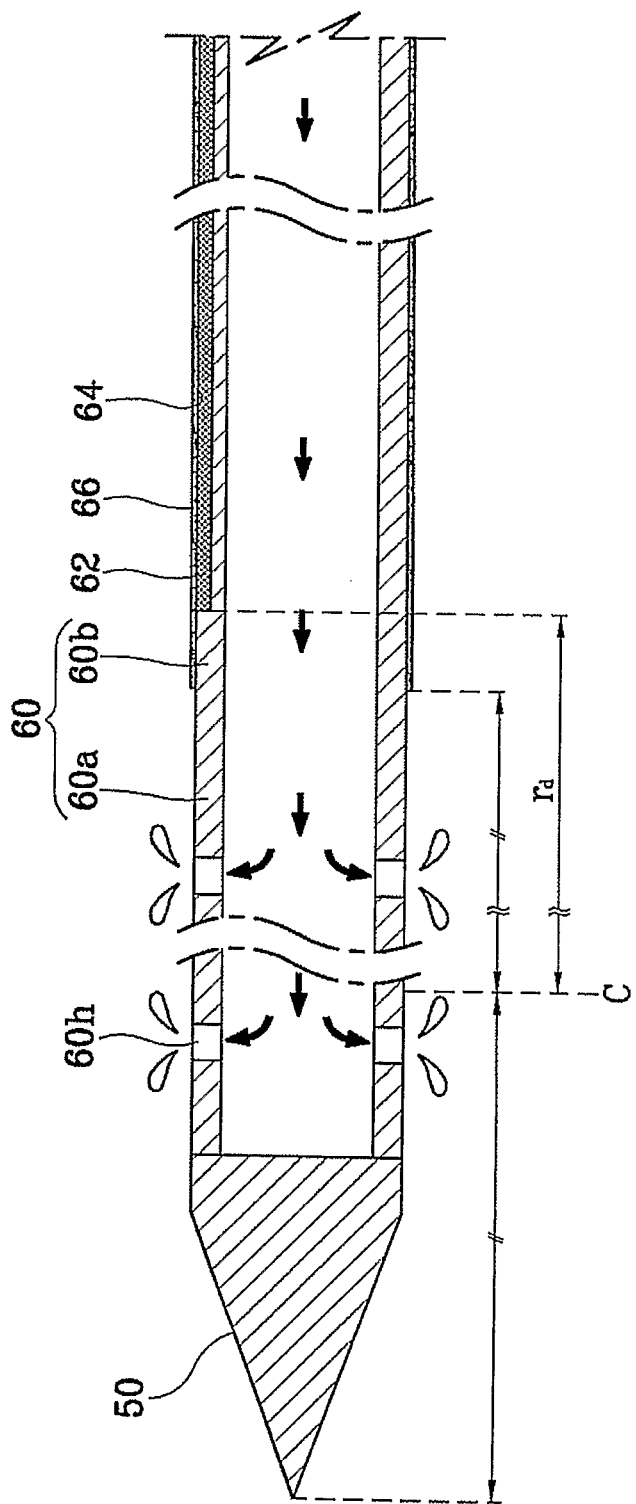
FIG. 11 is a side-sectional view illustrating the electrode for radiofrequency tissue ablation in accordance with the fifth embodiment of the present invention.

FIGS. 10 and 11 are a disassembly perspective view and a side-sectional view illustrating an electrode for radiofrequency tissue ablation in accordance with a fifth embodiment of the present invention.

In accordance with the fifth embodiment of the present invention, referring to FIGS. 10 and 11, the hollow electrode 60 is thicker than the general hollow electrode. The closed end 50 is connected to one end of the hollow electrode 60. The mounting groove 64 is formed long in the length direction with a predetermined gap from the closed end 50. The temperature sensor 62 and the electric wire are installed on the mounting groove 64 to be connected to the control unit. The insulation member 66 is inserted onto the outer circumference of the closed end 50 to cover the mounting groove 64. Therefore, the part of the hollow electrode 60 adjacent to the closed end 50 generates radiofrequency electric energy, thereby coagulating and necrotizing the peripheral tissue. A saline solution is injected into the hollow electrode 60 and the plurality of holes 60*h* are formed on the part of the hollow electrode 60 adjacent to the closed end 50, so that the saline solution can be discharged to the tissue contacting the closed end 50 and the part of the hollow electrode 60 generating radiofrequency electric energy. Thus, radiofrequency electric energy can be transmitted to the wide area.

Here, the hollow electrode 60 includes the non-insulation unit 60*a* which is not covered with the insulation member 66 and the insulation unit 60*b* covered with the insulation member 66. The non-insulation unit 60*a* and the insulation unit 60*b* are hollow tubes having the uniform inside and outside diameters. The plurality of holes 60*h* are formed on the non-insulation unit 60*a* in the circumference direction and the length direction at predetermined intervals.

Preferably, a low pressure saline solution is injected into the hollow electrode 60 to be directly discharged to the tissue through the holes 60*h* of the hollow electrode 60. The saline solution is a physiological saline solution which is not harmful to the tissue, for example, 0.9% saline solution, namely, an isotonic solution.

The closed end 50, the temperature sensor 62 and the insulation member 66 of the fifth embodiment are identical to those of the other embodiments, and thus detailed explanations thereof are omitted. The operation of the whole electrode will now be explained.

The electrode is selected in consideration of the installation position of the temperature sensor 62 according to the size of the ablation part, or the installation position of the temperature sensor 62 is set by sliding. The electrode is inserted into the tissue so that the center C of the length of the closed end 50 and the non-insulation unit 60*a* can be positioned at the center of the ablation part. Since the outer circumferences of the non-insulation unit 60*a* and the insulation unit 60*b* are smoothly connected to each other, the electrode can be easily inserted into the tissue without being hooked.

Thereafter, the control unit supplies radiofrequency energy to the electrode. The output is transmitted to the hollow electrode 60 and the closed end 50, so that the closed end 50 and the non-insulation unit 60*a* can generate radiofrequency electric energy in the closed end 50 and the non-insulation unit 60*a*. The peripheral tissue is coagulated and necrotized from the elliptical shape to the spherical shape by radiofrequency electric energy. At the same time, the low pressure refrigerants are sucked through the hollow electrode 60 and directly discharged to the tissue through the holes 60*h* formed on the non-insulation unit 60*a* adjacent to the closed end 50. Accordingly, the peripheral tissue is not carbonized, and the refrigerants are operated as conductors for transmitting radiofrequency electric energy to the whole tissues to which the refrigerants are sucked. As a result, a relatively large ablation part can be rapidly coagulated and necrotized.

Here, the control unit supplies the output so that the temperature sensed by the temperature sensor 62 can be maintained over about 55° C. for 5 minutes. If the above condition is satisfied, the control unit decides that the ablation part has been completely coagulated and necrotized, and stops supplying radiofrequency energy.

As discussed earlier, in accordance with the present invention, the high pressure refrigerants are sucked or discharged to/from the electrode and some of the refrigerants are discharged to the tissue for cooling, the high pressure refrigerants are sucked or discharged to/from the electrode for cooling, or the low pressure refrigerants are sucked to the electrode and wholly discharged to the tissue for cooling. Although the preferred embodiments of the present invention have been described, it is understood that the present invention should not be limited to these preferred embodiments but various changes and modifications can be made by one skilled in the art within the spirit and scope of the present invention as hereinafter claimed.

INDUSTRIAL APPLICABILITY

In the electrode for radiofrequency tissue ablation, at least one temperature sensor is mounted inside the insulation member on the outer circumference of the hollow electrode separated from the closed end generating radiofrequency electric energy by a predetermined gap. Generation of radiofrequency electric energy is controlled by adjusting the output supplied to the closed end and the hollow electrode according to the temperature sensed by the temperature sensor. Whether the target part of the tissue is completely coagulated and necrotized can be decided according to the temperature sensed by the temperature sensor. As a result, the specific part of the tissue can be precisely coagulated and necrotized by selectively using the electrodes whose temperature sensors are installed in different positions, which results in precise ablation.

The invention claimed is:

1. An apparatus for radiofrequency tissue ablation, comprising:

a conductive hollow electrode formed in an elongated hollow tube shape wherein a closed end is formed on one side of the hollow electrode to be inserted into a living body, wherein the conductive hollow electrode is divided into a non-insulation region extending from the closed end in a longitudinal direction of the conductive hollow electrode and an insulation region covered with a separate insulation member on an outer circumference of the conductive hollow electrode, wherein at least one groove extends on the outer circumference of the conductive hollow electrode in the insulation region thereof in the longitudinal direction of the conductive hollow electrode so that the at least one groove is covered with the separate insulation member, and wherein at least one temperature sensor is slidably installed in the at least one groove as well as between the conductive hollow electrode and the separate insulation member, for sensing temperature of a living tissue when in contact with the hollow electrode; and a control unit connected to the hollow electrode and the at least one temperature sensor, for determining when coagulation and necrosis of the living tissue has occurred based on the temperature sensed by the at least one temperature sensor, and controlling output supplied to the hollow electrode.

2. The apparatus of claim 1, wherein the separate insulation member is an insulation tube sheathing the insulation region of the conductive hollow electrode.

3. The apparatus of claim 1, wherein the at least one groove extends to a position in the insulation region spaced at least 5 mm from a boundary between the non-insulation region and the insulation region of the conductive hollow electrode.

4. The apparatus of claim 1, wherein the temperature sensor is adapted to be positioned within one radius of a desired ablation target from a longitudinal center of the non-insulation region of the conductive hollow electrode in the longitudinal direction of the conductive hollow electrode.

5. The apparatus of claim 1, wherein the at least one groove includes a plurality of grooves formed on the outer circumference of the conductive hollow electrode in the circumference direction at predetermined intervals, and the at least one temperature sensor includes a plurality of temperature sensors installed in the plurality of grooves, respectively.

6. The apparatus of claim 5, wherein the plurality of temperature sensors are configured to be spaced in different distances from a longitudinal center of the non-insulation region of the conductive hollow electrode in the longitudinal direction of the conductive hollow electrode.

* * * * *